(12) United States Patent
Mansour et al.

(10) Patent No.: US 8,567,400 B2
(45) Date of Patent: Oct. 29, 2013

(54) NON-INVASIVE BREATHING ASSISTANCE DEVICE WITH FLOW DIRECTOR

(75) Inventors: Khalid Mansour, Corona, CA (US); Eric Porteous, Corona, CA (US)

(73) Assignee: CareFusion 207, Inc., San Diego, CA (US)

(*) Notice: Subject to any disclaimer, the term of this patent is extended or adjusted under 35 U.S.C. 154(b) by 298 days.

(21) Appl. No.: 12/898,233

(22) Filed: Oct. 5, 2010

(65) Prior Publication Data

US 2012/0080034 A1    Apr. 5, 2012

(51) Int. Cl.
| | | |
|---|---|---|
| A61M 16/00 | (2006.01) | |
| A61M 15/08 | (2006.01) | |
| A62B 7/00 | (2006.01) | |
| A62B 9/00 | (2006.01) | |

(52) U.S. Cl.
USPC ............. 128/204.25; 128/204.18; 128/207.18

(58) Field of Classification Search
USPC ............. 128/201.22, 201.28, 204.18, 204.25, 128/205.25, 206.21, 206.28, 207.13, 128/207.18, 911
See application file for complete search history.

(56) References Cited

U.S. PATENT DOCUMENTS

| | | |
|---|---|---|
| 4,248,218 A | 2/1981 | Fischer |
| 4,262,665 A | 4/1981 | Roalstad et al. |
| 4,274,406 A | 6/1981 | Bartholomew |
| 4,681,100 A | 7/1987 | Brychta et al. |
| 4,782,832 A | 11/1988 | Trimble et al. |
| 4,821,736 A | 4/1989 | Watson |
| 4,915,105 A | 4/1990 | Lee |
| 5,046,491 A | 9/1991 | Derrick |
| 5,113,857 A | 5/1992 | Dickerman et al. |
| 5,193,532 A | 3/1993 | Moa et al. |
| 5,231,979 A | 8/1993 | Rose et al. |
| 5,451,190 A | 9/1995 | Liardet |
| 5,477,852 A | 12/1995 | Landis et al. |
| 5,687,715 A | 11/1997 | Landis et al. |
| 5,806,516 A | 9/1998 | Beattie |
| 5,975,077 A | 11/1999 | Hofstetter et al. |
| 6,119,694 A | 9/2000 | Correa et al. |
| 6,595,215 B2 | 7/2003 | Wood |
| 6,769,432 B1 | 8/2004 | Keifer |
| 6,863,069 B2 | 3/2005 | Wood |
| 6,997,187 B2 | 2/2006 | Wood et al. |
| 7,000,613 B2 | 2/2006 | Wood et al. |
| 7,152,604 B2 | 12/2006 | Hickle et al. |

(Continued)

OTHER PUBLICATIONS

ISA/KR, International Search Report and Written Opinion for International Application No. PCT/US2011/054782, 5 pages, May 22, 2012.

Primary Examiner — Melanie Hand
Assistant Examiner — Mark K Han
(74) Attorney, Agent, or Firm — McDermott Will & Emery LLP

(57) ABSTRACT

An nCPAP device for assisting patient breathing includes a generator body forming an inlet, a chamber, and first and second flow circuits. The chamber directs pressurized gas from the inlet to the flow circuits. The flow circuits each include a first and second jets, a flow director and an exhaust conduit. The jets emit a jetstream into the flow director in a direction of a patient side thereof. In some embodiments, the flow director forms a first tapered wall section directing inhaled air toward the patient and a second tapered wall section directing exhaled air toward the exhaust conduit. The generator body requires reduced driving pressures to achieve target CPAP levels and reduces total imposed WOB as compared to conventional designs.

27 Claims, 9 Drawing Sheets

(56) References Cited

U.S. PATENT DOCUMENTS

| Patent/Publication | Date | Inventor |
|---|---|---|
| 7,156,096 B2 | 1/2007 | Landis |
| 7,191,781 B2 | 3/2007 | Wood |
| 7,219,669 B1 | 5/2007 | Lovell et al. |
| 7,353,826 B2 | 4/2008 | Sleeper et al. |
| 7,578,294 B2 | 8/2009 | Pierro et al. |
| 2002/0053347 A1 | 5/2002 | Ziaee |
| 2003/0000527 A1 | 1/2003 | Stenzler et al. |
| 2003/0047185 A1 | 3/2003 | Olsen et al. |
| 2003/0079749 A1 | 5/2003 | Strickland et al. |
| 2003/0200970 A1 | 10/2003 | Stenzler et al. |
| 2004/0065330 A1 | 4/2004 | Landis |
| 2004/0244804 A1 | 12/2004 | Olsen et al. |
| 2005/0011524 A1 | 1/2005 | Thomlinson et al. |
| 2005/0133039 A1 | 6/2005 | Wood |
| 2005/0199242 A1 | 9/2005 | Matula, Jr. et al. |
| 2005/0241644 A1 | 11/2005 | Gunaratnam et al. |
| 2006/0042631 A1 | 3/2006 | Martin et al. |
| 2006/0042634 A1 | 3/2006 | Nalagatla et al. |
| 2006/0130840 A1 | 6/2006 | Porat et al. |
| 2006/0174887 A1 | 8/2006 | Chandran et al. |
| 2006/0180149 A1 | 8/2006 | Matarasso |
| 2006/0231103 A1 | 10/2006 | Matula, Jr. et al. |
| 2006/0266361 A1 | 11/2006 | Hernandez |
| 2007/0074724 A1 * | 4/2007 | Duquette et al. .......... 128/204.18 |
| 2007/0125379 A1 | 6/2007 | Pierro et al. |
| 2007/0125384 A1 | 6/2007 | Zollinger et al. |
| 2007/0125387 A1 | 6/2007 | Zollinger et al. |
| 2007/0163600 A1 | 7/2007 | Hoffman |
| 2007/0175473 A1 | 8/2007 | Lewis et al. |
| 2007/0186930 A1 | 8/2007 | Davidson et al. |
| 2007/0246043 A1 | 10/2007 | Kwok et al. |
| 2008/0295846 A1 * | 12/2008 | Han et al. ................. 128/207.13 |
| 2009/0165799 A1 | 7/2009 | Duquette et al. |
| 2010/0108073 A1 | 5/2010 | Zollinger et al. |
| 2010/0252044 A1 | 10/2010 | Duquette et al. |

* cited by examiner

NON-INVASIVE BREATHING ASSISTANCE DEVICE WITH FLOW DIRECTOR

BACKGROUND

The present disclosure generally relates to devices and methods for generating and delivering continuous positive airway pressure therapy or other non-invasive breathing assistance to patients, such as infants. More particularly, the present disclosure relates to variable flow, nasal continuous positive airway pressure systems, devices, and methods with reduced driving pressure requirements and improved work-of-breathing.

Continuous positive airway pressure (CPAP) therapy has been employed for many years to treat patients experiencing respiratory difficulties and/or insufficiencies. In addition, CPAP therapy can beneficially assist patients with under-developed lungs (in particular, infants and especially premature infants or neonates) by preventing lung collapse during exhalation and assisting lung expansion during inhalation.

In general terms, CPAP therapy entails the continuous transmission of positive pressure into the lungs of a spontaneously breathing patient throughout the respiratory cycle. CPAP can be delivered to the patient using a variety of patient interface devices, for example an endotracheal tube or nasal cannula. With infants, however, it is more desirable to employ a non-invasive patient interface device, in particular one that interfaces directly or indirectly with the nasal airways via the patient's nares. Such systems are commonly referred as nasal continuous positive airway pressure (nCPAP) systems.

In theory, the CPAP system should deliver a constant, stable pressure (above atmospheric pressure) to the patient's airways. With conventional CPAP systems, a relatively constant and continuous flow of gas (e.g., air, oxygen, etc.) is delivered into the patient's airways, with this airflow creating a pressure within the patient's lungs via a restriction placed on outflow from the patient. Unfortunately, this continuous flow can have an adverse effect on the patient's respiratory synchrony. More particularly, the patient is required to exhale against the incoming gas, thus increasing the patient's work-of-breathing. Control valves can be employed to better accommodate inspiratory and expiratory stages of a patient's breathing cycle (e.g., controlling gas flow into the system and/or altering an extent of restriction from outflow from the system). However, for many patients, especially infants, this approach is less than satisfactory as the patient's required work-of-breathing is quite high. That is to say, it is essentially impossible for a control valve system to accurately replicate the actual respiratory cycles experienced by the patient, such that the patient will consistently be required to exhale against the high momentum, incoming gas, as well as against the resistance of the control valve(s). For an infant with underdeveloped lungs, even a slight increase in the required work-of-breathing may render the CPAP system in question impractical.

More recently, nCPAP systems have been developed that incorporate a variable flow concept in combination with separate channels for inspiratory and expiratory gas to and from the patient. When the patient inhales, the incoming gas takes the path of least resistance and is directed to the patient's airways. Upon expiration, the gas again takes the path of least resistance and goes out an exhaust port, thus reducing resistance during the expiratory phase of breathing. For example, the Infant Flow™ system, available from CareFusion, Inc., of San Diego, Calif., includes a variable flow CPAP generating device (or "CPAP generator") that causes the direction of the supply gas to change with the infant's breathing patterns while maintaining a constant pressure throughout the respiratory cycle. The Infant Flow CPAP generator converts supplied gas into jet streams (one for each naris), with a momentum of the gas jet creating a positive pressure inside the patient's lungs, in accordance with known jet pump principles. To accommodate expiratory flow from the patient, the Infant Flow CPAP generator relies upon what the manufacturer's literature lists as a "fluidic flip" effect. The expiratory airflow from the patient applies a pressure onto the incoming jet steam flow. It has been theorized that due to the coanda effect, the expiratory airflow causes the jet stream flow to deflect, thus triggering a fluidic flip of the incoming jet flow. As a result, the jet stream and the expiratory airflow readily proceed to the exhaust port, thus reducing the patient's required work-of-breathing. While quite promising, the jets streams in these devices maintain a relatively high momentum that may not be easily overcome by the patient's expiratory breathing, especially with infants. Moreover, it is often desirable to reduce the amount of pressure that needs to be supplied to the CPAP generator, thereby simplifying the structure of the associated jet pump, which in turn may have benefits with respect to reduced size, energy consumption, sound, complexity and cost.

In light of the above, a need exists for an improved nCPAP system, device, and method.

SUMMARY

Some aspects in accordance with principles of the present disclosure relate to a nasal continuous positive airway pressure (nCPAP) device for assisting patient breathing. The device includes a generator body forming an inlet, a chamber, and first and second flow circuits. The inlet is configured for fluid connection to a source of pressurized gas. The chamber is fluidly connected to the inlet. The first and second flow circuits are fluidly connected to the chamber and each include first and second jets and a flow director. The jets define an inlet end and an outlet end, with the inlet end being fluidly connected to the chamber. The outlet end is adapted to emit a gas jet stream into the flow director. The flow director has or defines a jet side fluidly connected to the outlet end of the jets, and a naris or patient side opposite the jet side. The patient side forms or is connected to a nasal prong or mask for interfacing with a patient's naris. Each of the flow directors forms a first tapered wall section having a decreasing diameter in a direction of the patient side, and a second tapered wall section defining a decreasing diameter from the patient side toward the jet side. The second tapered wall section facilitates diversion of the jet stream by exhaled airflow during the expiratory phase of operation. During use, pressurized gas delivered to the chamber via the inlet is converted to a fixed flow jet stream by the jets, creating CPAP in each of the channels. Further, the generator body establishes an inspiratory flow pattern during an inspiratory stage of breathing and an expiratory flow pattern during an expiratory stage of breathing. With the expiratory flow pattern, exhaled air from the patient side of each of the flow directors is directed by the second tapered wall section to cause at least a portion of the jet stream flow to divert to, and exhaust from, an exhaust conduit. In a particular embodiment, each of the tapered wall sections forms a funnel-shaped annular ring that tapers in diameter from an inlet end to an outlet end. The generator bodies of the present disclosure require reduced inlet or driving pressures to achieve desired therapeutic CPAP levels and/or reduce total imposed work-of-breathing by the patient.

Other aspects in accordance with principles of the present disclosure relate to a nasal continuous positive airway pressure (nCPAP) system including a generator body, a patient interface piece, and a source of gas. The generator body defines an inlet, a chamber, and first and second flow circuits. The chamber is fluidly connected to the inlet, and the flow circuits are fluidly connected to the chamber. Each of the flow circuits includes first and second jets and a flow director. In one embodiment, the jets impinge with one another and create a combined jet stream from pressurized gas in the chamber, and direct the jet stream into a jet side of the flow director to an opposite, patient side. The patient interface includes first and second prongs fluidly connected to the patient side of the flow directors, respectively, and is configured for fluid connection to a patient's nares. Finally, the source of gas is fluidly connected to the inlet of the generator body and provides a continuous flow of pressurized gas. Upon connection of the interface piece to the patient's nares and of the source of gas to the inlet, a fixed amount of jet stream flow is established in each of the flow directors by the corresponding jet. A momentum of the jet streams deliver CPAP to the patient. In an inspiratory phase of operation, the jet stream flow is delivered to the patient's nares via the corresponding flow director. In an expiratory phase, exhaled air from the patient nares diverts the jet stream flow from the jets and is exhausted through a corresponding exhaust conduit.

Yet other aspects in accordance with principles of the present disclosure relate to a method for establishing and delivering a continuous positive airway pressure to a patient. The method includes fluidly connecting a generator body to nares of the patient. The generator body forms first and second flow circuits each including first and second jets, a flow director and an exhaust conduit. The flow director includes first and second tapered wall sections. Gas from a source of pressurized gas is forced to an inlet end of each of the jets. A jet stream from each of the jets is directed toward the patient's nares via the flow director to establish a continuous positive airway pressure in the patient's airway. During periods of patient exhalation, exhaled air is directed by the second tapered wall section to divert the jet stream to the exhaust conduit at which the jet stream is exhausted from the generator body.

DETAILED DESCRIPTION

Figure 1:
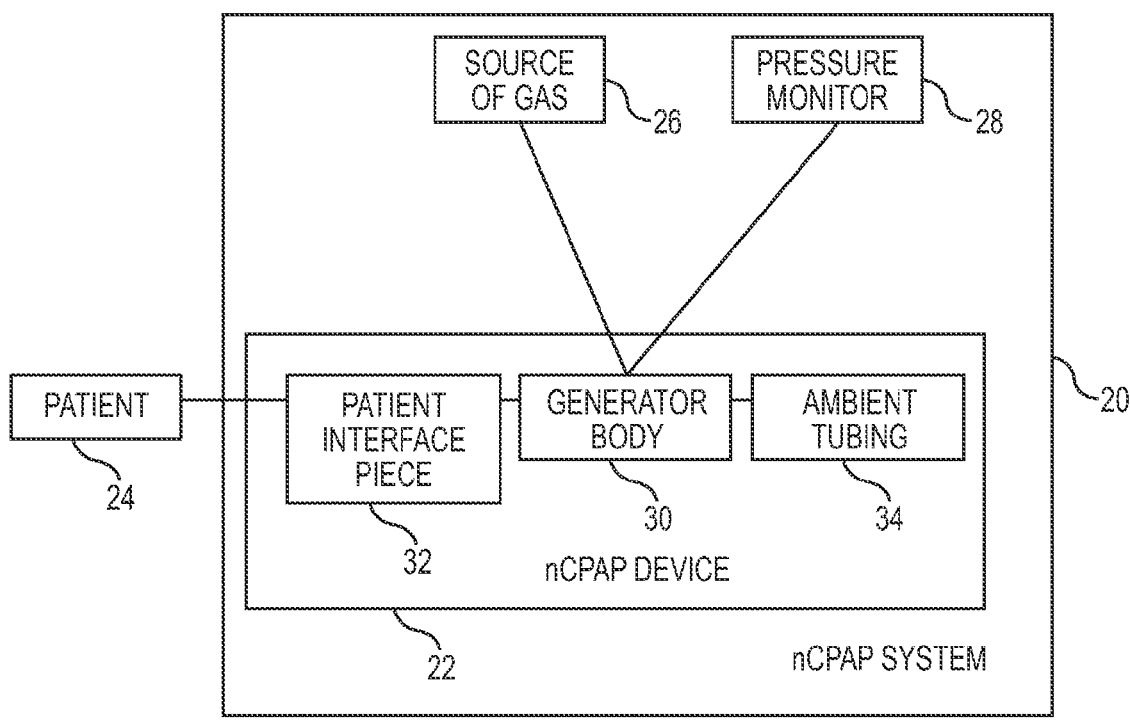
FIG. 1 is a block diagram illustrating one embodiment of a nasal continuous positive airway pressure system including an nCPAP device in accordance with principles of the present disclosure.

One embodiment of a nasal continuous positive airway pressure (nCPAP) system 20 incorporating an nCPAP device 22 in accordance with principles of the present disclosure is shown in block form in FIG. 1. In general terms, the system 20 is adapted to provide CPAP therapy to a patient 24, and includes the nCPAP device 22 and a source of pressurized gas 26. The nCPAP system 20 can further optionally include a pressure monitor 28. The nCPAP device 22 is described in greater detail below, and generally includes a generator body 30 and a patient interface piece 32. Optionally, ambient air tubing 34 can also be provided. The generator body 30 is fluidly connected to the patient interface 32 and the optional ambient air tubing 34, with the patient interface piece 32 being adapted to establish fluid communication with the patient's 24 nasal airways. The source of pressurized gas 26 provides the generator body 30 with a continuous flow of gas (e.g., air and/or oxygen). Where provided, the pressure monitor 28 is also fluidly connected to the generator body 30 and samples or measures pressure therein. During use, the generator body 30 acts upon gas from the source 26 to generate and deliver a continuous positive airway pressure to the patient 24 via the patient interface piece 32. As the patient 24 exhales, the exhaled air readily flows through the patient interface piece 32/generator body 30, and is exhausted from the nCPAP device 22 as described below.

Figure 2:
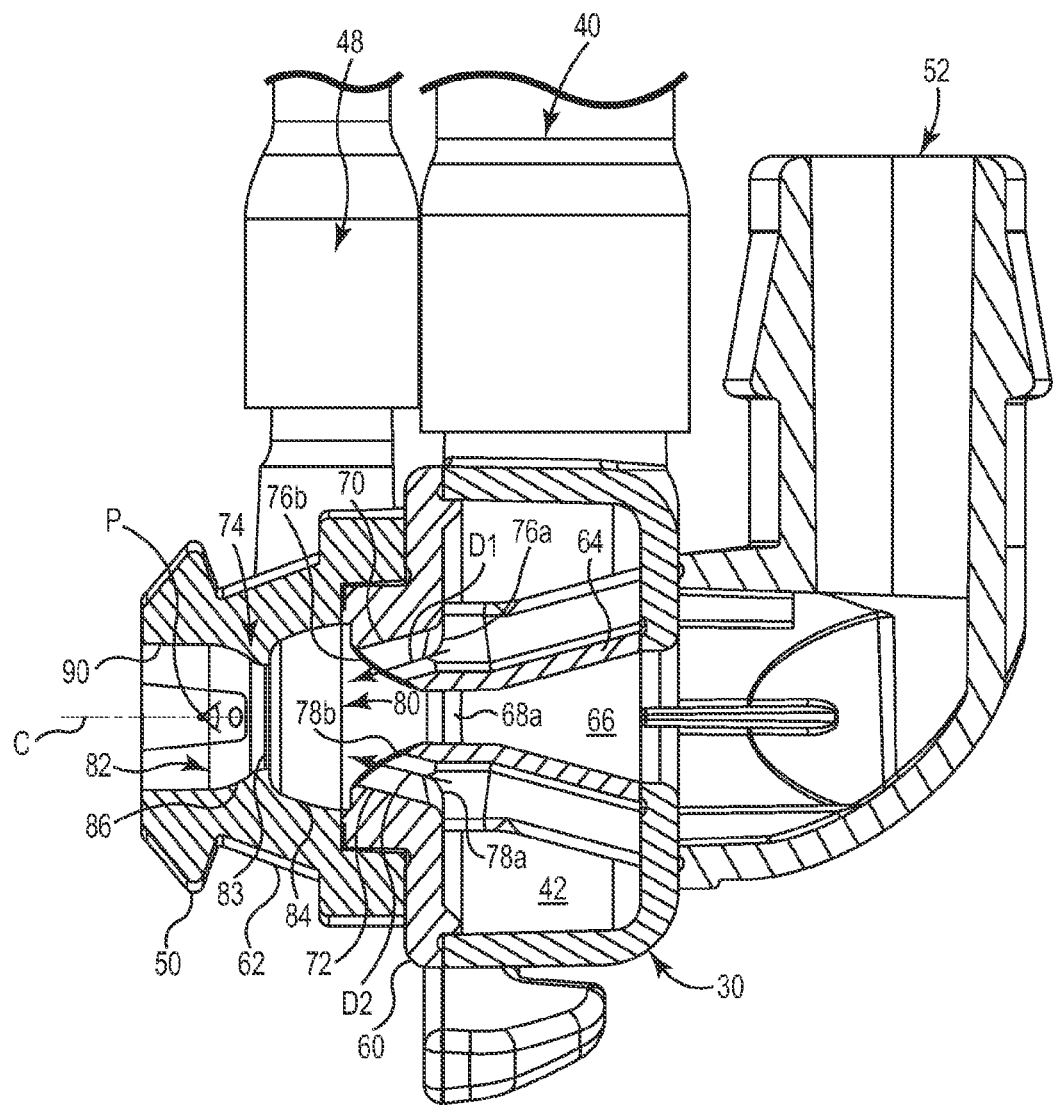
FIG. 2 is a side, sectional view of a generator body in accordance with principles of the present disclosure and useful with the nCPAP device of FIG. 1.
Figure 3:
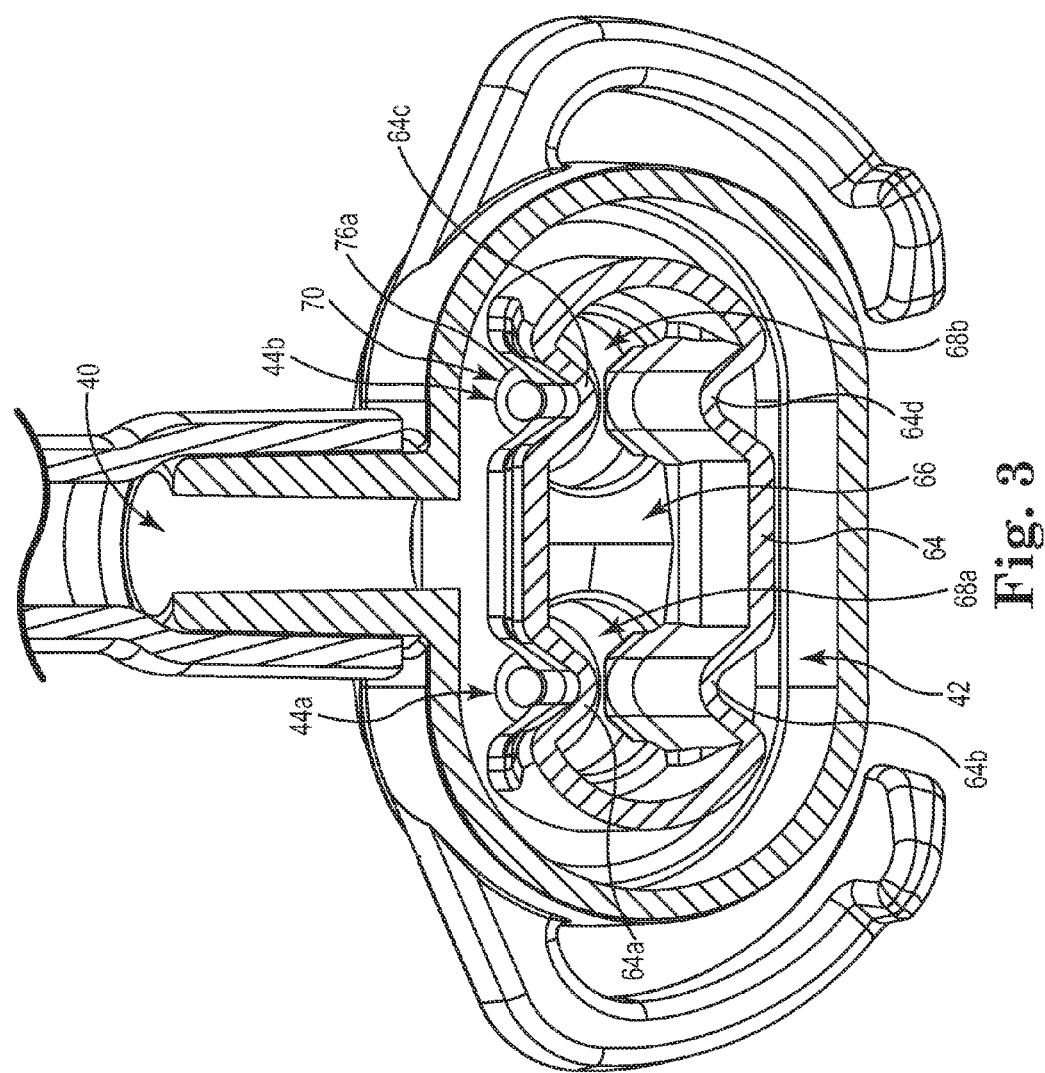
FIG. 3 is a perspective cross-sectional view of the generator body of FIG. 2.

One embodiment of the generator body 30 in accordance with principles of the present disclosure is shown in FIGS. 2 and 3. In general terms, the generator body 30 is configured to establish CPAP via separate channels for inspiratory and expiratory flow of gas to and from the patient 24 (FIG. 1). With this in mind, the generator body 30 forms or defines a supply gas inlet 40, a chamber 42, and first and second flow circuits 44a, 44b (referenced generally in FIG. 3; the first flow circuit 44a being shown fully in FIG. 2). In general terms, the inlet 40 is configured for fluid connection to the source of pressurized gas 26 (FIG. 1), and directs incoming gas into the chamber 42. The flow circuits 44a, 44b are fluidly connected to the chamber 42. Thus, gas flow provided at the inlet 40 is directed through the chamber 42 and then toward the patient via the flow circuits 44a, 44b. In this regard, and as described in greater detail below, the flow circuits 44a, 44b incorporate one or more features that promote exhausting of supplied gas and exhaled air during an expiratory phase of operation with minimal patient work of breathing effort. The generator body 30 can incorporate additional, optional components, such as a pressure monitoring port 48, an exterior flange 50, an exhaust port 52, etc.

In some embodiments, the generator body 30 can have a two (or more) piece construction, including a supply section 60 and a circuit section 62. The sections 60, 62 can be separately formed (e.g., molded plastic) and assembled to another, with the supply section 60 forming the inlet 40 and the chamber 42. The circuit section 62 forms the flow circuits 44a, 44b. Alternatively, other constructions are also envisioned, such as integrally constructing the generator body 30 as a single, homogenous body.

The inlet 40 can assume various forms (e.g., size and shape) appropriate for fluid connection to a supply tube (not shown) extending from the source of gas 26 (FIG. 1). The chamber 42 is fluidly connected to the supply inlet 40 and is fluidly open to the first and second flow circuits 44a, 44b, with FIG. 3 illustrating fluid communication between the chamber 42 and the first flow circuits 44a and 44b. Effectively, then, an internal wall 64 (referenced generally in FIG. 3) provides or forms a manifold that is fluidly open to the chamber 42 and the flow circuits 44a, 44b. On an internal side of wall 64, an exhaust conduit 66 is formed that carries air from the patient to the exhaust port 52. Each of the flow circuits 44a and 44b includes an exhaust pathway 68*a* and 68*b* that is fluidly coupled to the exhaust conduit 66.

The first and second flow circuits 44*a*, 44*b* are, in some embodiments, identical such that the following description of the first flow circuit 44*a* is equally applicable to the second flow circuit 44*b*. The first flow circuit 44*a* includes or defines first and second jets 70, 72 and a bi-directional flow director 74. In the embodiment illustrated in FIG. 3, the internal wall 64 is annularly shaped and includes diverging portions 64*a*-*d* that accommodates jets of the first and second flow circuits. Jet 70 includes an opening defining an inlet end 76*a* that is fluidly coupled to chamber 42 and an outlet end 76*b* fluidly coupled to flow director 74. Similarly, jet 72 includes an opening defining an inlet end 78*a* that is fluidly coupled to chamber 42 and an outlet end 78*b* fluidly coupled to flow director 74. The jets 70, 72 are angled toward each other and direct fluid from chamber 42 to the flow director 74. In one embodiment, an angle between the jets is approximately 60°, although other angles can be used. In any event, the jets 70 and 72 are angled toward each other such that the flow from each is concentrated at a jet impingement point P.

Flow director 74 includes a first, jet side 80, a second, patient side 82 and a transition point 83. The jet side 80 defines a first tapered wall section 84 that directs flow from the jets 70 and 72 toward the patient. In particular, the jet side tapered wall section 84 concentrates a fluid path from the jets 70 and 72 toward the patient (e.g., the patient's nares) to achieve a desired flow to the patient. The jet side tapered wall section 84 provides a smooth transition of flow from the jets 70 and 72. In particular, the tapered wall section 84 tapers in diameter toward the transition point 83. In turn, the patient side 82 defines a second tapered wall section 86 that directs exhaled air from the patient to the exhaust conduit 66 through the corresponding exhaust pathway 68*a*. This concentration from the patient side wall section 86 will flip gas flow from the jets 70 and 72 back toward exhaust conduit 66.

Transition point 83 defines a reduced aperture, sized to allow passage of each jet flow from jets 70 and 72, while each jet flow is undisturbed and organized during the inspiratory phase. During the expiratory phase, the patient's breath acts upon each jet flow, causing each jet flow to diverge and thus each jet flow is redirected by transition point 83 along wall section 84 to the exhaust conduit 66.

Figure 4:
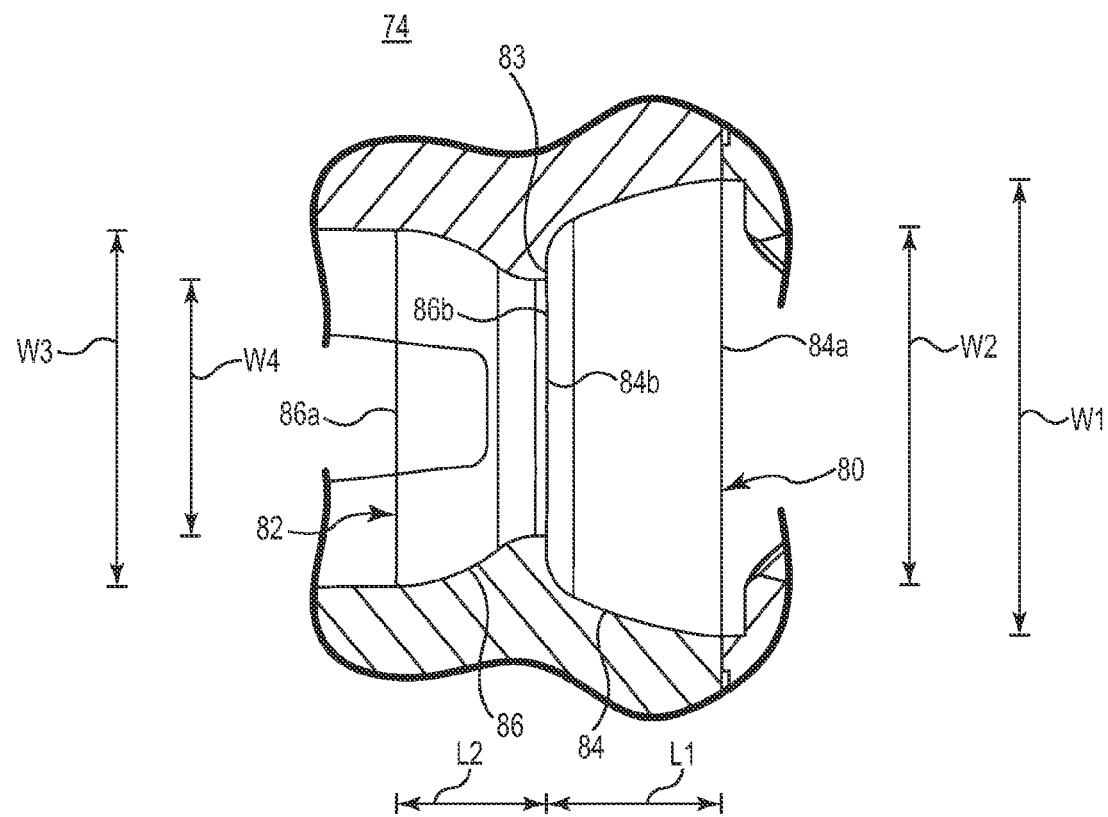
FIG. 4 is a side view of a flow director of the generator body of FIG. 2.

With particular reference to FIG. 4, tapered wall section 84 includes an inlet end 84*a* of a first diameter (or width in cross section) W1 and an outlet end 84*b* of a second diameter (or width in cross section) W2. Tapered wall section 84 is herein embodied as a continuous, funnel-shaped annular ring, although other configurations for wall section 84 are contemplated. For example, wall section 84 can be non-continuous and/or includes linear sections as desired. In any event, a diameter of tapered wall section 84 decreases from inlet end 84*a* (opposite patient side 82) to outlet end 84*b* (proximate patient side 82 at transition point 83) along a length L1 of the tapered wall section 84. As illustrated herein, the wall section 84 is curved along length L1 to create the funnel shape of the wall section 84. In one embodiment, W1 is approximately 0.20 inches, W2 is approximately 0.16 inches and L1 is approximately 0.075 inches. As such, a ratio of W1 to L1 is approximately 2.7 and a ratio of W2 to L1 is approximately 2.1. Furthermore, a ratio of W1 to W2 is approximately 1.25. Other dimensions for W1, W2 and L1 can be used in a range from 0.15-0.25 inches, W2 can be in a range from 0.12-0.2 inches and L1 can be in a range from 0.05 inches to 0.10 inches. The ratio of S1 to L1 can be in a range from 2.0 to 3.5, the ratio of W2 to L1 can be in a range from 1.5 to 2.75 and a ratio of W1 to W2 can be in a range from 1.10 to 1.60.

In a similar manner, tapered wall section 86 includes an inlet end 86*a* having a first diameter (or width in cross section) W3 and an outlet end 86*b* having a second diameter (or width in cross section) W4 at transition point 83. Tapered wall section 86 is also embodied herein as a continuous, funnel-shaped annular ring, although other configurations are contemplated. For example, wall section 86 can be non-continuous and/or include linear sections as desired. Wall section 86 decreases in diameter from inlet end 86*a* (opposite jet side 80) to outlet end 86*b* (proximate jet side 80 at transition point 83) along a length L2 of the tapered wall section 86. As illustrated herein, the wall section 86 is curved along length L2 to create the funnel shape of the wall section 86. In one embodiment, W3 is approximately 0.15 inches, W4 is approximately 0.11 inches and L2 is approximately 0.14 inches. As such, a ratio of W3 to L2 is approximately 1.1 and a ratio of W4 to L2 is approximately 0.79. Furthermore, a ratio of W3 to W4 is approximately 1.36. Other dimensions for W3, W4 and L2 can be used. For example, W3 can be in a range from 0.10 inches to 0.20 inches, W4 can be in a range from 0.08 inches to 0.15 inches and L2 can be in a range from 0.10 inches to 0.20 inches. The ratio of W3 to L2 can be in a range from 0.825 to 1.375, a ratio of W4 to L2 can be in a range from 0.60 to 1.0 and a ratio of W3 to W4 can be in a range from 1.1 to 1.5. Additionally, W2 is of a greater dimension than W4. In other embodiments, W2 can be of a smaller dimension than W4 or W2 and W4 can be substantially equal.

With reference back to FIG. 2, flow director 74 terminates in a tube 90 that directs flow to a patient interface. The tube 90 defines an axial centerline C. As shown, the jets 70 and 72 are fluidly open to the tube 90 at the jet side 80 and are arranged in a non-parallel fashion relative to the axial centerline C, as well as to each other. The jets 70 and 72 each define a flow direction axis $D_1$, $D_2$. The flow direction axes $D_1$, $D_2$ corresponds with the central axis defined by the respective jets 70 and 72, and define the direction in which fluid exits from the respective outlet end 76*b*, 78*b* thereof. With this in mind, in one embodiment, the jets 70 and 72 are arranged such that the flow direction axes $D_1$, $D_2$ intersect or impinge upon each other approximately at the axial centerline C. That is to say, the jets 70 and 72 are symmetrically arranged about the axial centerline C after the transition point 83. To this end, and in one embodiment, the jets 70 and 72 are angularly oriented relative to the axial centerline C such that the flow direction axes $D_1$, $D_2$ combine to define an included angle θ in the range of 40°-80°, preferably 50°-70°, more preferably approximately 60°) (±1°). In addition, each of the jets 70 and 72 are configured to generate jetstream fluid flow via a constricted fluid flow path from the inlet end 76*a*, 78*a* to the outlet end 78*a*, 78*b*. Regardless, fluid jet streams produced by the jets 70 and 72 impinge upon one another and combine approximately at the axial centerline C.

During operation, pressurized gas (e.g., from the source of gas 26 (FIG. 1)) is provided to the chamber 42 via the supply inlet 40. The supplied gas is forced to the flow circuits 44*a* and 44*b*. As shown for the first flow circuit 44*a* in FIG. 5, the jets 70, 72 convert the gas flow to jet streams J that are directed into the flow director 74. Pressurized gas is delivered to the chamber 42 via the supply inlet 40 and is directed toward the flow circuits 44. The jet streams J combine to form a jet stream N, which establishes a continuous positive airway pressure within the flow director 74 (e.g., the jet stream N momentum is converted into pressure) that is applied to the patient side 82, and thus the patient. At least a portion of the jet stream N flow is directed through the flow director 74 and delivered to/inhaled by the patient at the patient side 82. Relative to the jet stream N, first tapered wall section 84 defines a tapering diameter to transition point 83. As a result of the taper, a portion of the jet stream N experiences a recirculating flow R along the first tapered wall section 84. The recirculating flow R, in turn, diverts an excess portion (represented by arrow E in FIG. 5) of the jet stream N to the exhaust pathway 68a and exhaust conduit 66 as exhaust flow.

Figure 5:
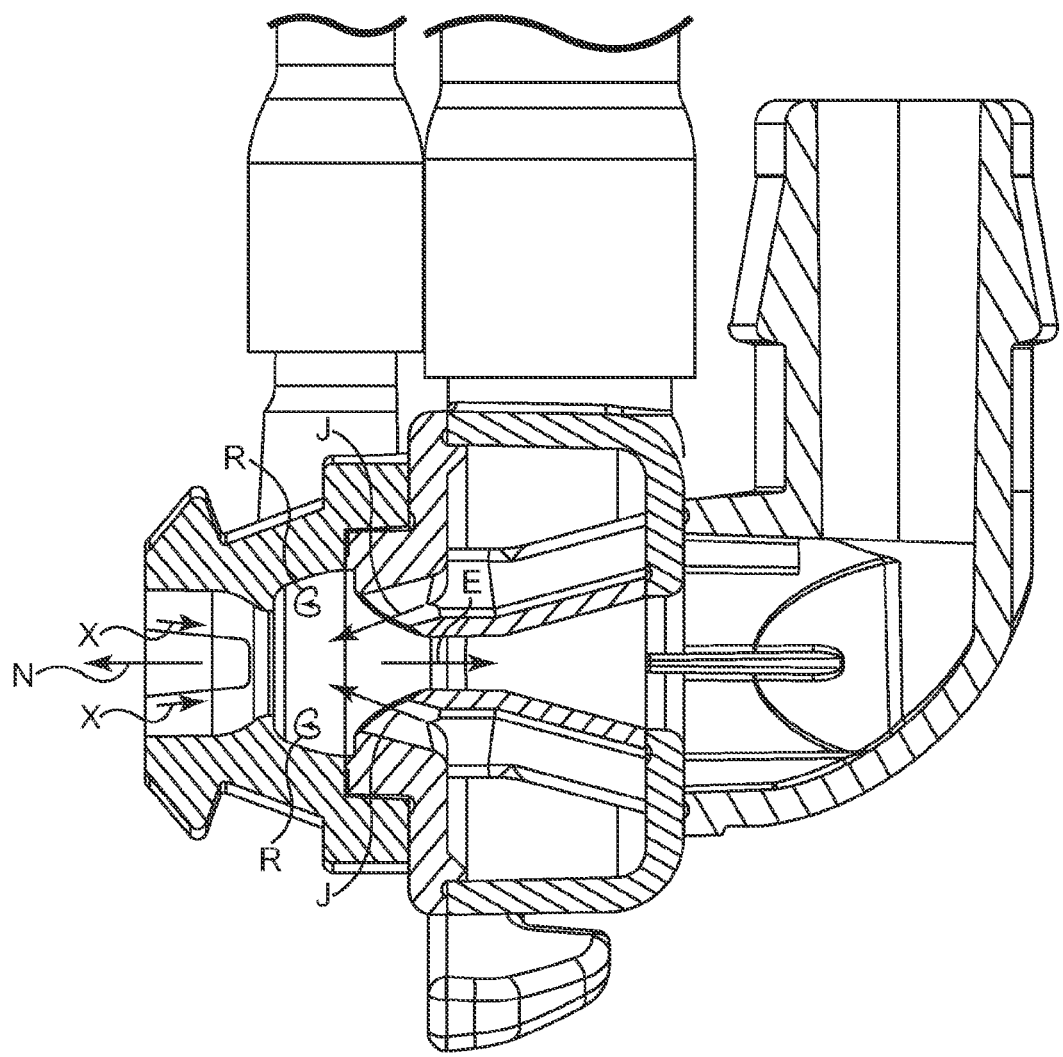
FIG. 5 is a side, sectional view of the generator body of FIG. 2 showing inspiratory and expiratory phases.

During the expiratory phase of operation shown in FIG. 5, the jet stream N continues to be generated by and emitted from the jets 70 and 72 into the flow director 74, maintaining the continuous positive airway pressure delivered to the patient due to the jet stream's N momentum. Exhaled air (represented by arrows X in FIG. 5) enters the flow director 74 at the patient side 82, and acts upon the jet stream N flow. In this regard, relative to a flow direction of the exhaled air X, the second tapered wall section 86 defines a tapering diameter that increases a magnitude of the velocity of the exhaled air X at the transition point 83. Further, the second tapered wall section 86 effectively "focuses" a portion of the exhaled air X toward the jet stream N flow. This focused, flow diverts or "turns" the jet stream N toward the exhaust pathway 68a and exhaust conduit 66. The jet stream N, as well as a substantial portion of the exhaled air X, exhausts from the generator body 30 via the exhaust conduit 66 and as shown by arrow E. Thus, the exhaust conduit 66, the tapered wall sections 84, 86, and a geometry of the jet stream N combine to establish flow patterns that minimize resistance to the exhaled air X and the corresponding patient work-of-breathing.

It has surprisingly been found that the wall sections described above in combination with one or more geometry characteristics render the generator body 30 capable of establishing desired CPAP levels at low driving pressures and with minimal patient work-of-breathing. For example, in some embodiments, the jets 70 and 72 have a diameter (and thus a diameter of the resultant jet stream N) on the order of 0.0445 inches, optionally in a range from 0.04-0.05 inches. In other embodiments, alternative dimensions can be utilized based on other factors such as an angle for jets 70 and 72, length of jets 70 and 72, distance from jets 70 and 72 to flow director 74, etc.

Returning to FIGS. 2 and 3, the optional pressure monitoring port 48 is located to tap or sample air pressure within the generator body 30. The pressure monitoring port 48 can be fluidly connected to one or both of the flow circuits 44a, 44b, and provides a surface appropriate for connection to monitoring tubing (not shown) extending to the pressure monitor 28 (FIG. 1). In other embodiments, the pressure monitoring port 48 can be omitted.

The optional exterior flange 50 provides a surface for mounting of various other components, such as the patient interface 32 described below. In other embodiments, the flange 50 can be omitted.

The generator body 30 can incorporate additional features facilitating connection with other components of the nCPAP system 20 (FIG. 1) and/or desired functioning. For example, the tube bodies 90 associated with the flow circuits 44a, 44b can form or define exterior rings adapted to promote a secured, sealed attachment with the patient interface piece 32 (FIG. 1).

Figure 6:
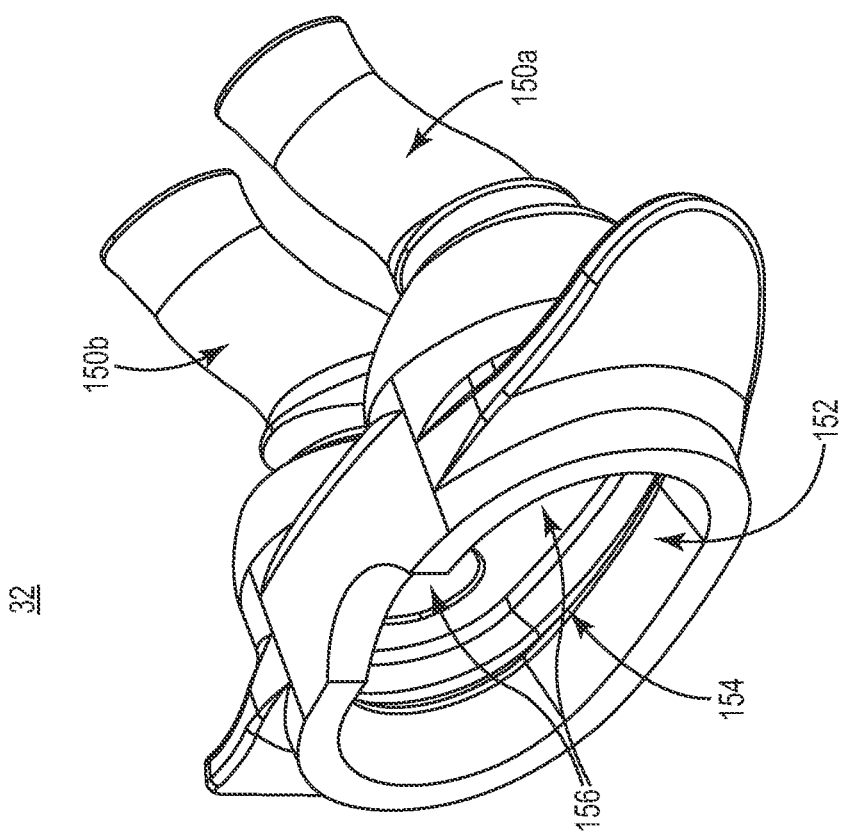
FIG. 6 is a perspective view of a patient interface piece useful with the system of FIG. 1.

Returning to FIG. 1, the patient interface 32 useful with the generator bodies of the present disclosure can assume various forms. For example, FIG. 6 generally illustrates one exemplary embodiment of the patient interface piece 32 that includes a pair of nasal prongs 150a, 150b projecting from a base 152. The base 152 can incorporate additional features, such as a sealing flange 154. With reference between FIGS. 2 and 6, the base 152 is generally sized and shaped for assembly to the generator body 30, for example via a perimeter shape including a shape of the flange 50. The base 152 forms a pair of apertures 156 sized to be fluidly coupled with respective ones of the fluid circuit tubular bodies 90. The nasal prongs 150a, 150b may be of any size and shape as are suitable for interacting with the patient's nares, and are fluidly open to the apertures 156. Assembly of the patient interface piece 32 to the generator body 30 generally entails establishing a fluid connection between the nasal prongs 150a, 150b, and the patient side 82 of a respective one of the flow circuits 44a, 44b. In other embodiments, the patient interface 32 can be a nasal mask.

Figure 7:
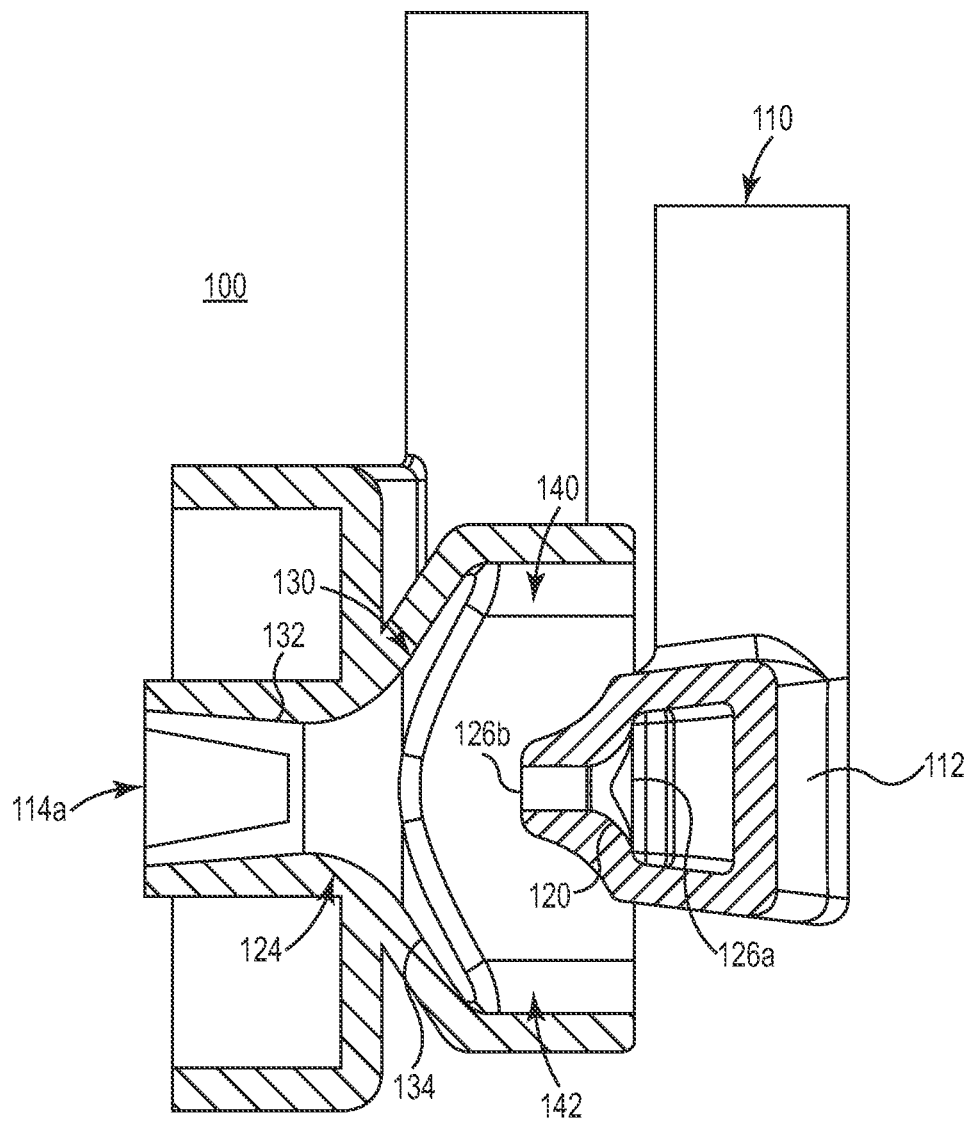
FIG. 7 is a side, sectional view of a generator body in accordance with principles of the present disclosure and useful with the nCPAP device of FIG. 1.
Figure 8:
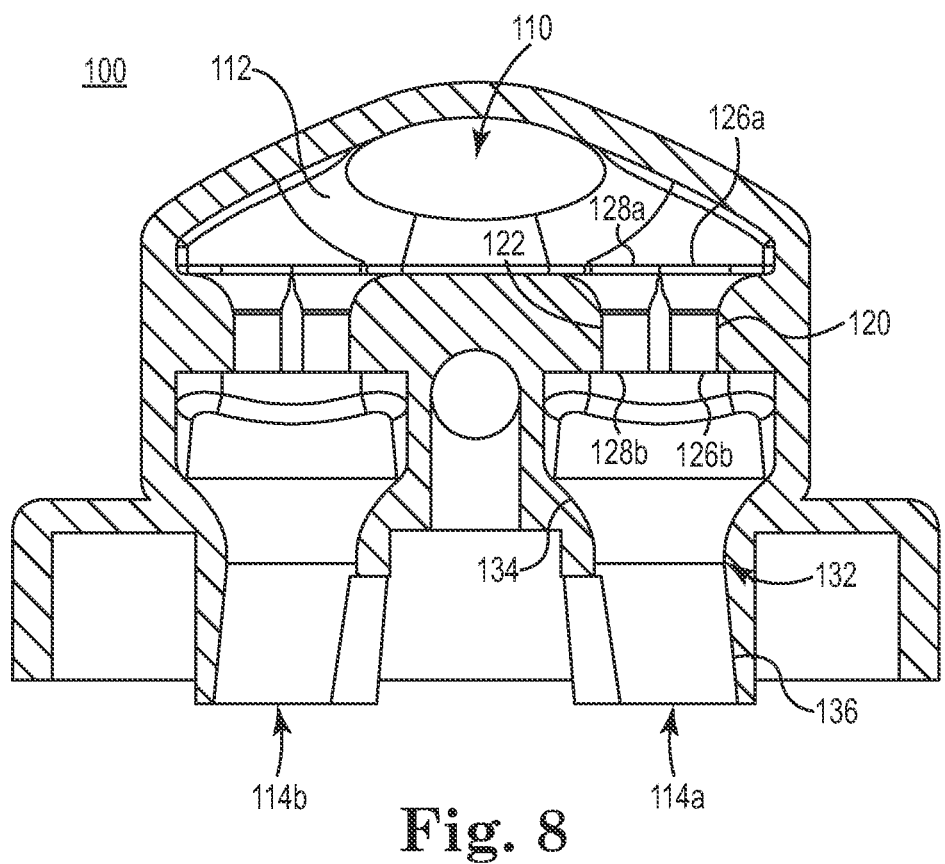
FIG. 8 is a front, sectional view of the generator body of FIG. 7.

Another embodiment of a generator body (such as generator body 30 of FIG. 1) in accordance with principles of the present disclosure is shown in FIGS. 7 and 8 as generator body 100. In general terms, the generator body 100 is configured to establish CPAP via separate channels for inspiratory and expiratory flow of gas to and from the patient 24 (FIG. 1). With this in mind, the generator body 100 forms or defines a supply gas inlet 110, a chamber 112, and first and second flow circuits 114a, 114b (referenced generally). In general terms, the inlet 110 is configured for fluid connection to the source of pressurized gas 26 (FIG. 1), and directs incoming gas into the chamber 112. The flow circuits 114a, 114b are fluidly connected to the chamber 112. Thus, gas flow provided at the inlet 110 is directed through the chamber 112 and then toward the patient via the flow circuits 114a, 114b. In this regard, and as described in greater detail below, the flow circuits 114a, 114b incorporate one or more features that promote exhausting of supplied gas and exhaled air during an expiratory phase of operation with minimal patient work of breathing effort. The generator body 100 can incorporate additional, optional components, such as a pressure monitoring port, an exterior flange, etc., as discussed above.

The inlet 110 can assume various forms (e.g., size and shape) appropriate for fluid connection to a supply tube (not shown) extending from the source of gas 26 (FIG. 1). The chamber 112 is fluidly connected to the supply inlet 110 and is fluidly open to the first and second flow circuits 114a, 114b, with FIG. 8 illustrating fluid communication between the chamber 112 and the first flow circuits 114a and 114b.

The first and second flow circuits 114a, 114b are, in some embodiments, identical such that the following description of the first flow circuit 114a is equally applicable to the second flow circuit 114b. The first flow circuit 114a includes or defines first and second jets 120, 122 and a bi-directional flow director 124. Jet 120 includes an opening defining an inlet end 126a that is fluidly coupled to chamber 112 and an outlet end 126b fluidly coupled to flow director 124. Similarly, jet 122 includes an opening defining an inlet end 128a that is fluidly coupled to chamber 112 and an outlet end 128b fluidly coupled to flow director 124. The jets 120, 122 are parallel with respect to each other and direct fluid from chamber 112 to the flow director 124. The inlet ends 126a, 128a are of a larger diameter than outlet ends 128a, 128b, so as to concentrate flow from chamber 112 to flow director 124.

Flow director 124 includes a first, jet side 130 and, a second, patient side 132. The jet side 130 defines a first tapered wall section 134 that directs flow from the jets 120 and 122 toward the patient. In particular, the jet side tapered wall section 134 concentrates a fluid path from the jets 120 and 122 toward the patient (e.g., the patient's nares) to achieve a desired flow to the patient. The jet side tapered wall section 134 provides a smooth transition of flow from the jets 120 and 122. In turn, the patient side 132 defines a second tapered wall section 136 that directs exhaled air from the patient to upper and lower exhaust ports 140 and 142. In particular, the exhaled air from patient side tapered wall section 136 is concentrated at the jet outlets 126b, 128b. This concentration from the patient side tapered wall section 136 will flip gas flow from the jets 120 and 122 toward the exhaust ports 140 and 142.

During operation, pressurized gas (e.g., from the source of gas 26 (FIG. 1)) is provided to the chamber 112 via the supply inlet 110. The supplied gas is forced to the flow circuits 114a and 114b. As shown for the first flow circuit 114a in FIG. 9, the jets 120, 122 convert the gas flow to jet streams J that are directed into the flow director 124. The jet streams J combine to form a jet stream N, which establishes a continuous positive airway pressure within the flow director 124 (e.g., the jet stream N momentum is converted into pressure) that is applied to the patient side 132, and thus the patient. At least a portion of the jet stream N flow is directed through the flow director 124 and delivered to/inhaled by the patient at the patient side 132. Relative to the jet stream N, first tapered wall section 134 defines a tapering diameter. A portion of the jet stream N experiences a recirculating flow R along the first tapered wall section 134. The recirculating flow R, in turn, diverts an excess portion (represented by arrow E in FIG. 9) of the jet stream N to the exhaust ports 140 and 142 as exhaust flow.

Figure 9:
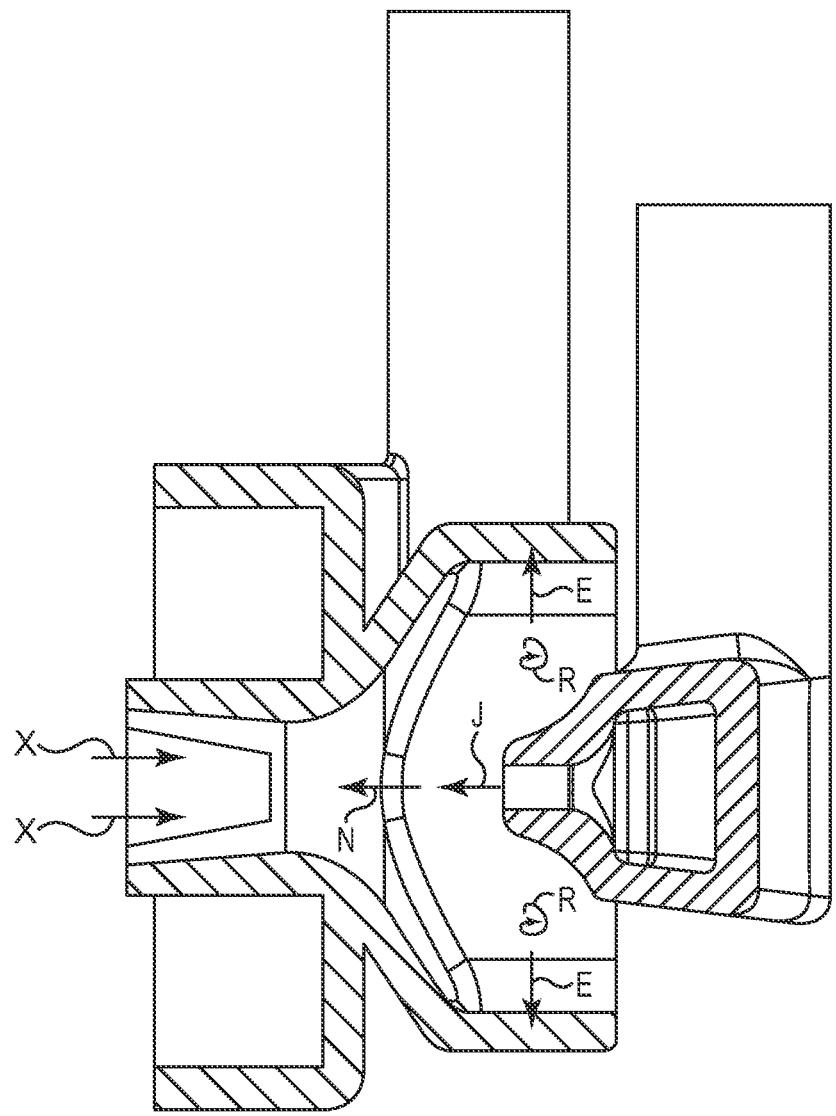
FIG. 9 is a side, sectional view of the generator body of FIG. 7 showing inspiratory and expiratory phases.

During the expiratory phase of operation shown in FIG. 9, the jet stream N continues to be generated by and emitted from the jets 120 and 122 into the flow director 124, maintaining the continuous positive airway pressure delivered to the patient due to the jet stream's N momentum. Exhaled air (represented by arrows X in FIG. 9) enters the flow director 124 at the patient side 130, and acts upon the jet stream N flow. In this regard, relative to a flow direction of the exhaled air X, the second tapered wall section 136 defines a tapering diameter that increases the velocity magnitude of the exhaled air X. Further, the second tapered wall section 136 effectively "focuses" a portion of the exhaled air X toward the jet stream N flow. This focused, flow diverts or "turns" the jet stream N toward the exhaust ports 140 and 142. The jet stream N, as well as a substantial portion of the exhaled air X, exhausts from the generator body 100 via the exhaust ports 140 and 142. Thus, the exhaust ports 140, 142, the 134, 136, and a geometry of the jet stream N combine to establish flow patterns that minimize resistance to the exhaled air X and the corresponding patient work-of-breathing.

The CPAP devices, and related systems and methods, of the present disclosure provide a marked improvement over previous designs. In particular, the generator bodies envisioned by the present disclosure have reduced driving pressure requirements necessary for delivering desired levels of CPAP, as well as reduced total imposed WOB properties. Further, by incorporating low profile ports and condensed jet stream features, the generator bodies of the present disclosure can be relatively small as compared to existing designs.

Although the present disclosure has been described with reference to preferred embodiments, workers skilled in the art will recognize that changes can be made in form and detail without departing from the spirit and scope of the present disclosure.

What is claimed is:

1. A nasal continuous positive airway pressure device for use in a CPAP system to assist patient breathing, the device comprising:
   a generator body forming:
      an inlet for fluid connection to a source of pressurized gas,
      a chamber fluidly connected to the inlet,
      first and second flow circuits fluidly connected to the chamber,
      each of the flow circuits including:
         first and second jets each defining an inlet end and an outlet end, the inlet end fluidly connected to the chamber,
         a flow director defining:
            a jet side fluidly connected to the outlet ends of the jets,
            a patient side opposite the jet side for directing gas from the patient's naris,
            a first wall section between the jet and patient sides, the first wall section having an inlet end and an outlet end, the first wall section tapering in diameter toward the patient side,
            a second wall section between the first wall section and the patient side, the second wall section having an inlet end and an outlet end, the second wall section tapering in diameter toward the jet side, the outlet end of the second wall section substantially abutting the outlet end of the first wall section.

2. The device of claim 1, wherein the first wall section is curved in a direction from the jet side to the patient side.

3. The device of claim 1, wherein the second wall section is curved in a direction from the patient side to the jet side.

4. The device of claim 1, wherein the first wall section is a funnel-shaped annular ring.

5. The device of claim 1, wherein the second wall section is a funnel-shaped annular ring.

6. The device of claim 1, wherein the first wall section defines a first diameter near the inlet end and a second diameter near the outlet end, and the second wall section defines a third diameter near the inlet end and a fourth diameter near the outlet end, wherein the second diameter is greater than the fourth diameter.

7. The device of claim 1, wherein each flow circuit further defines an exhaust pathway.

8. The device of claim 7, wherein the exhaust pathway is positioned between first and second jets of the corresponding flow circuit.

9. The device of claim 1, wherein the chamber is annular.

10. The device of claim 1, wherein for each flow circuit, the jets are non-parallel to one another.

11. The device of claim 1, wherein for each flow circuit, the jets are parallel to one another.

12. A nasal continuous positive airway pressure system for assisting patient breathing, the system comprising:
   a generator body forming:
      an inlet,
      a chamber fluidly connected to the inlet,
      first and second flow circuits fluidly connected to the chamber, each of the flow circuits including:
         first and second jets defining an inlet end and an outlet end, the inlet end fluidly connected to the chamber,
         a flow director having:
            a jet side fluidly connected to the outlet end of the jets,
            a patient side opposite the jet side,
            a first wall section between the jet side and patient side, the first wall section having an inlet end and an outlet end, the first wall section tapering in diameter toward the patient side,
            a second wall section between the first wall section and the patient side, the second wall section having an inlet end and an outlet end, the second wall section tapering in diameter toward the jet side, the outlet end of the second wall section substantially abutting the outlet end of the first wall section;

a patient interface piece fluidly connected to the patient side of the flow directors, respectively; and a source of pressurized gas fluidly connected to the inlet;

wherein upon securement of the patient interface piece to a patient's nares, the system is configured to generate a continuous positive airway pressure in the patient by delivering gas from the source of pressurized gas to the jets that in turn emits a gas jet stream within the corresponding flow director in a direction of the patient interface piece.

13. The system of claim 12, wherein the first wall section is curved in a direction from the jet side to the patient side.

14. The system of claim 12, wherein the second wall section is curved in a direction from the patient side to the jet side.

15. The system of claim 12, wherein the first wall section is a funnel-shaped annular ring.

16. The system of claim 12, wherein the second wall section is a funnel-shaped annular ring.

17. The system of claim 12, wherein the first wall section defines a first diameter near the inlet end and a second diameter near the outlet end, and the second wall section defines a third diameter near the inlet end and a fourth diameter near the outlet end, wherein the second diameter is greater than the fourth diameter.

18. The system of claim 12, wherein each flow circuit further defines an exhaust pathway.

19. The system of claim 18, wherein the exhaust pathway is positioned between first and second jets of the corresponding flow circuit.

20. The system of claim 12, wherein the chamber is annular.

21. The system of claim 12, wherein for each flow circuit, the jets are non-parallel to one another.

22. The system of claim 12, wherein for each flow circuit, the jets are parallel to one another.

23. A method for establishing and delivering a continuous positive airway pressure to a patient, the method comprising:

fluidly connecting a generator body to nares of the patient, the generator body forming first and second flow circuits each including: first and second jets, a flow director forming first and second wall sections, and an exhaust pathway;

forcing gas from a source of pressurized gas to an inlet end of each of the jets;

directing a jet stream from each of the jets toward the patient's nares via the corresponding flow director to establish a continuous positive airway pressure in the patient's airway;

during periods of patient inhalation, the jet stream delivering gas flow to the patient and establishing a recirculating flow along the first wall section; and during periods of patient exhalation, exhaled air from the patient being directed by the second wall section to divert the jet stream to the corresponding exhaust pathway, wherein the flow director includes a jet side and a patient side, wherein the first wall section is disposed between the jet side and the patient side, includes an inlet end and an outlet end, and defines a decreasing diameter in a direction from the jet side to the patient side, wherein the second wall section is disposed between the first wall section and the patient side, includes an inlet end and an outlet end, and defines a decreasing diameter in a direction from the patient side to the jet side, and wherein the outlet end of the second wall section substantially abuts the outlet end of the first wall section.

24. The method of claim 23, wherein the exhaust pathway is positioned between first and second jets of the corresponding flow circuit.

25. The method of claim 23, wherein a chamber of the generator body is annular.

26. The method of claim 23 wherein for each flow circuit, the jets are non-parallel to one another.

27. The method of claim 23, wherein for each flow circuit, the jets are parallel to one another.

* * * * *